United States Patent
Hettrick et al.

(10) Patent No.: US 12,350,028 B2
(45) Date of Patent: *Jul. 8, 2025

(54) SYSTEMS AND METHODS FOR ASSESSING EFFICACY OF RENAL NEUROMODULATION THERAPY

(71) Applicant: Medtronic Ireland Manufacturing Unlimited Company, Dublin (IE)

(72) Inventors: Douglas Hettrick, Andover, MN (US); Paul Coates, Corte Madera, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 86 days.

This patent is subject to a terminal disclaimer.

(21) Appl. No.: 18/298,414

(22) Filed: Apr. 11, 2023

(65) Prior Publication Data
US 2023/0240549 A1    Aug. 3, 2023

Related U.S. Application Data

(63) Continuation of application No. 16/121,472, filed on Sep. 4, 2018, now Pat. No. 11,633,120.

(51) Int. Cl.
*A61B 5/02* (2006.01)
*A61B 5/00* (2006.01)
(Continued)

(52) U.S. Cl.
CPC ............ *A61B 5/027* (2013.01); *A61B 5/0275* (2013.01); *A61B 5/4848* (2013.01);
(Continued)

(58) Field of Classification Search
CPC ..... A61B 5/027; A61B 5/0275; A61B 5/4848; A61B 18/1492; A61B 2018/00404; A61B 2018/00434; A61B 2018/00511; A61B 2018/00577; A61B 2018/00642; A61B 2018/00863; A61B 2018/00875;
(Continued)

(56) References Cited

U.S. PATENT DOCUMENTS

| | | | | |
|---|---|---|---|---|
| 5,453,576 A | * | 9/1995 | Krivitski | A61B 5/0275 600/481 |
| 2009/0131930 A1 | * | 5/2009 | Gelbart | A61B 18/1492 606/41 |
| 2016/0256076 A1 | * | 9/2016 | Kassab | A61B 5/6853 |

* cited by examiner

*Primary Examiner* — Michael F Peffley
*Assistant Examiner* — Bo Ouyang
(74) *Attorney, Agent, or Firm* — Shumaker & Sieffert, P.A.

(57) ABSTRACT

Systems and methods for performing and assessing neuromodulation therapy are disclosed herein. One method for assessing the efficacy of neuromodulation therapy includes positioning a neuromodulation catheter at a target site within a renal blood vessel of a human patient and delivering neuromodulation energy at the target site with the neuromodulation catheter. The method can further include obtaining a measurement related to a blood flow rate through the renal blood vessel via the neuromodulation catheter. The measurement can be compared to a baseline measurement related to the blood flow rate through the renal blood vessel to assess the efficacy of the neuromodulation therapy. In some embodiments, the baseline and post-neuromodulation measurements are obtained by injecting an indicator fluid into the renal blood vessel upstream of the target site and detecting a transient change in vessel impedance caused by the indicator fluid.

20 Claims, 11 Drawing Sheets

(51) Int. Cl.
*A61B 5/027* (2006.01)
*A61B 5/0275* (2006.01)
*A61B 18/14* (2006.01)
*A61B 18/00* (2006.01)
*A61B 18/02* (2006.01)
*A61B 18/16* (2006.01)

(52) U.S. Cl.
CPC ..................... *A61B 18/1492* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00863* (2013.01); *A61B 2018/00875* (2013.01); *A61B 2018/0212* (2013.01); *A61B 2018/1435* (2013.01); *A61B 2018/167* (2013.01)

(58) Field of Classification Search
CPC .... A61B 2018/0212; A61B 2018/1435; A61B 2018/167
See application file for complete search history.

SYSTEMS AND METHODS FOR ASSESSING EFFICACY OF RENAL NEUROMODULATION THERAPY

This application is a continuation of U.S. patent application Ser. No. 16/121,472, filed Sep. 4, 2018, and entitled, "SYSTEMS AND METHODS FOR ASSESSING EFFICACY OF RENAL NEUROMODULATION THERAPY," the entire disclosure of which is incorporated herein by reference.

TECHNICAL FIELD

The present technology is generally related to neuromodulation. In particular, various embodiments of the present technology are related to systems and methods for measuring blood flow through a renal blood vessel to assess the efficacy of neuromodulation therapy.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
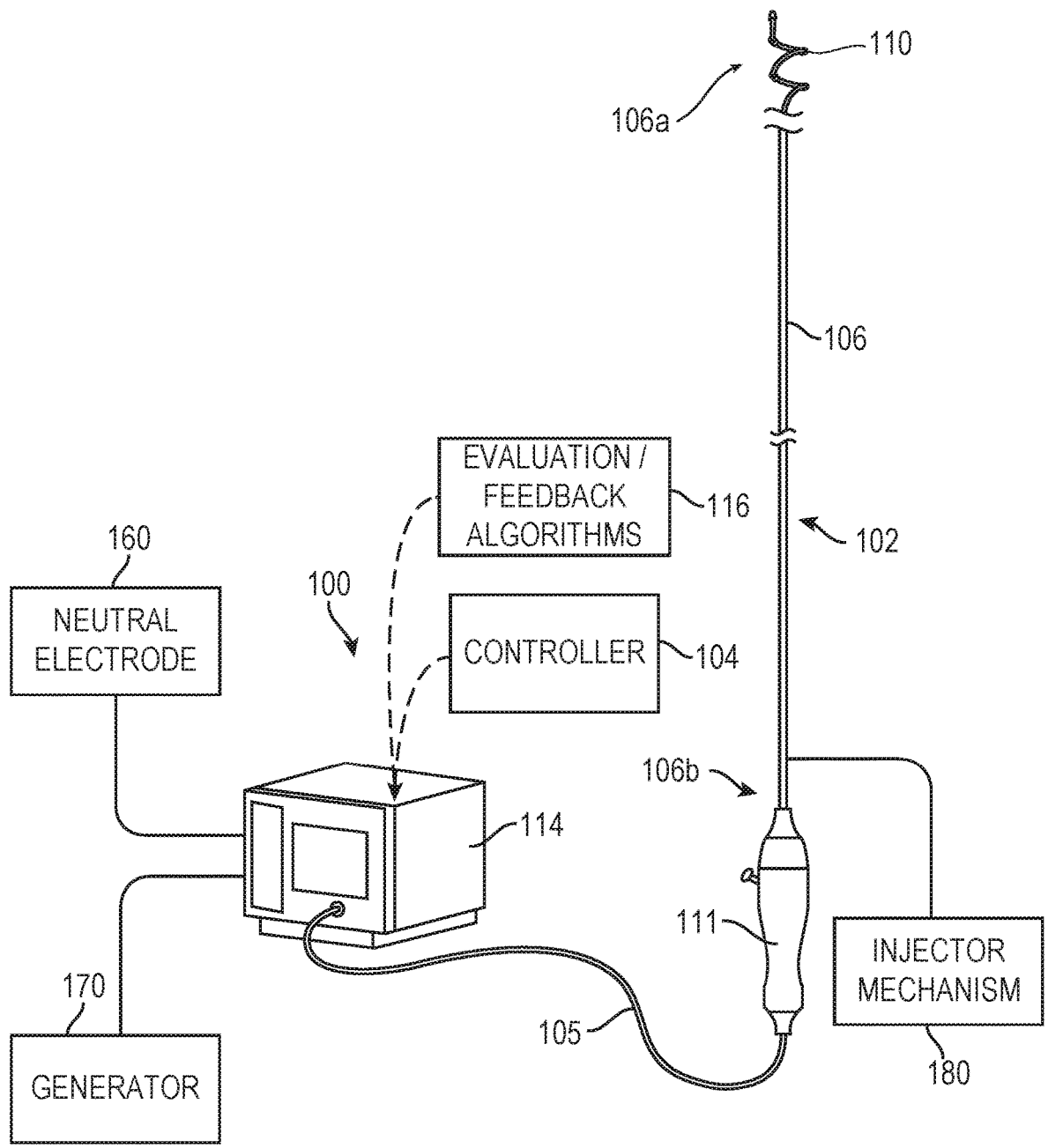
FIG. 1 is a partially schematic illustration of a neuromodulation system configured in accordance with an embodiment of the present technology.

Systems and methods in accordance with embodiments of the present technology are directed to obtaining measurements related to a blood flow rate through a renal blood vessel before, during, and/or after a neuromodulation procedure, such as a renal denervation procedure, to periprocedurally assess the likely efficacy of the neuromodulation procedure (e.g., to determine if adequate denervation has been achieved). The disclosed techniques can be used, for example, to assess a particular patient's likelihood of deriving a therapeutic benefit from delivered neuromodulation energy.

Research suggests that renal nerve destruction—such as that caused by a successful neuromodulation procedure—can cause an instantaneous or nearly instantaneous vasodilation (e.g., relaxation) of the renal vascular bed, especially within the arterial microcirculation. Vasodilation can lead to a detectable change in renal arterial hemodynamics such as an increase in renal blood flow and/or decrease in renal arterial resistance (when combined with simultaneous measurements of arterial pressure). Therefore, measuring the change in renal blood flow or renal arterial resistance—or a related value—resulting from a neuromodulation procedure is expected to provide periprocedural information about the success (or lack thereof) of the neuromodulation procedure.

Currently, there are only limited means available for a practitioner performing a neuromodulation procedure to know immediately after performing the procedure whether the procedure was successful (e.g., caused a sufficient amount of renal nerve destruction). Indeed, because of the complexity of the sympathetic nervous system response to neuromodulation, the practitioner must often wait weeks or months to determine the success of a neuromodulation procedure. Moreover, current techniques for measuring the blood flow within (or arterial resistance of) a renal blood vessel require other devices and procedures in addition to those employed during the neuromodulation procedure, and can be slow, expensive, and relatively inaccurate.

In contrast with conventional systems and techniques, in several of the embodiments described below, a neuromodulation system can include a neuromodulation catheter configured to both (i) deliver neuromodulation energy at a target site in a renal blood vessel and (ii) detect one or more measurements related to a blood flow rate through the renal blood vessel. A controller can receive the measurements from the neuromodulation catheter and compare the measurements to a baseline measurement to automatically determine a change in the blood flow rate through the renal blood vessel resulting from neuromodulation energy delivered via the neuromodulation catheter. The determined change in the blood flow rate can be used to assess the efficacy of the delivered neuromodulation energy. For example, as set forth above, an increase in the blood flow rate can indicate that a successful level or amount of renal nerve destruction has been achieved. Accordingly, systems configured in accordance with the present technology are expected to provide for rapid periprocedural assessment of the efficacy of a neuromodulation procedure by detecting a blood flow rate or related value through the renal blood vessel in which neuromodulation is carried out.

Specific details of several embodiments of the present technology are described herein with reference to FIGS. 1-13. Although many of the embodiments are described with respect to devices, systems, and methods for intravascular renal neuromodulation, other applications and other embodiments in addition to those described herein are within the scope of the present technology. For example, at least some embodiments of the present technology may be useful for intravascular non-renal neuromodulation and/or use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

I. SELECTED EMBODIMENTS OF NEUROMODULATION SYSTEMS

Figure 2A:
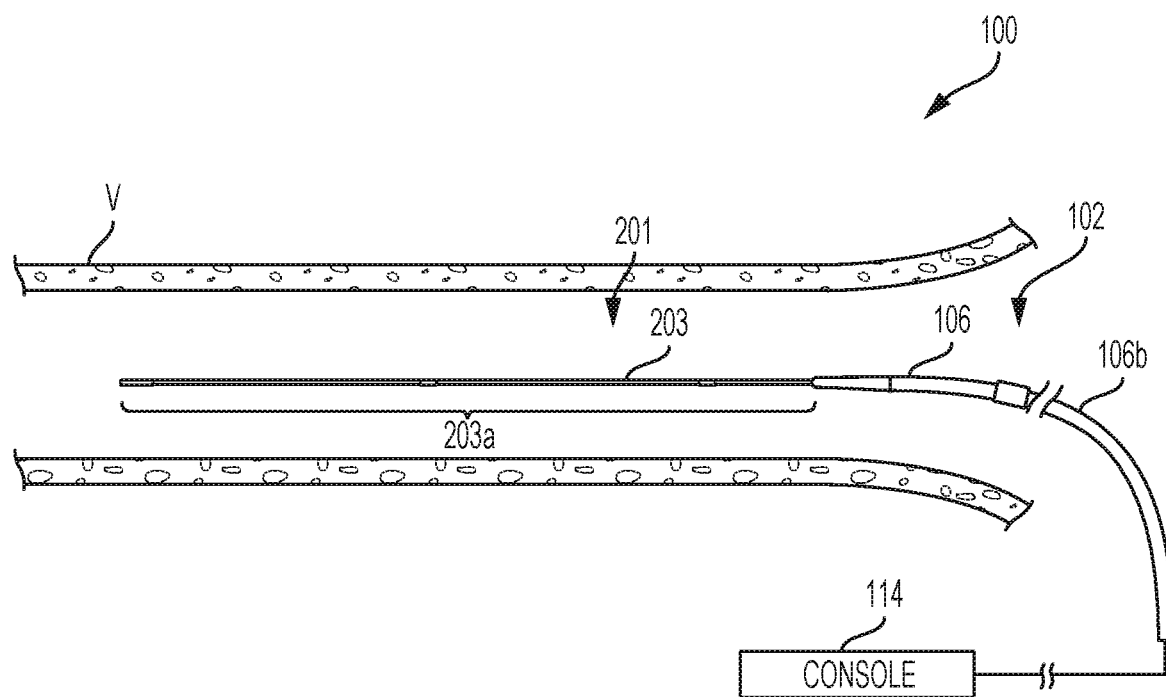
FIG. 2A is a partially schematic side view of the neuromodulation system of FIG. 1 with a distal portion of a guidewire positioned within a blood vessel of a human patient in accordance with an embodiment of the present technology.
Figure 2B:
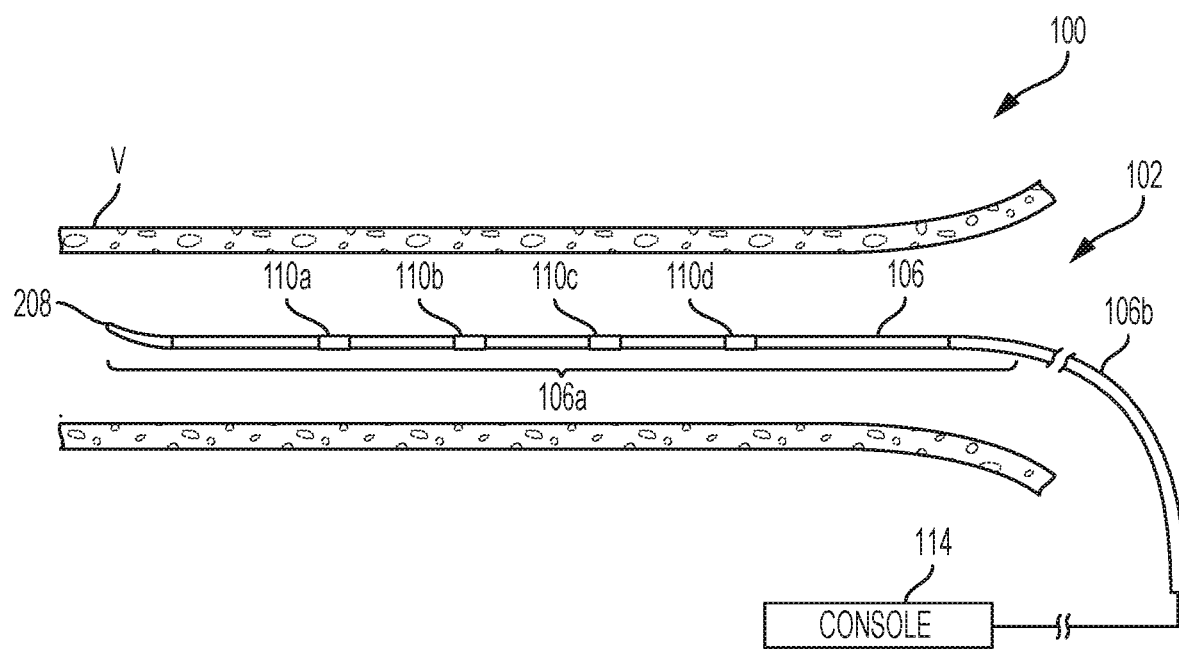
FIGS. 2B and 2C are partially schematic side views of the neuromodulation system of FIG. 1 with a distal portion of a neuromodulation catheter in a first state and a second state, respectively, within a blood vessel of a human patient in accordance with an embodiment of the present technology.
Figure 2C:
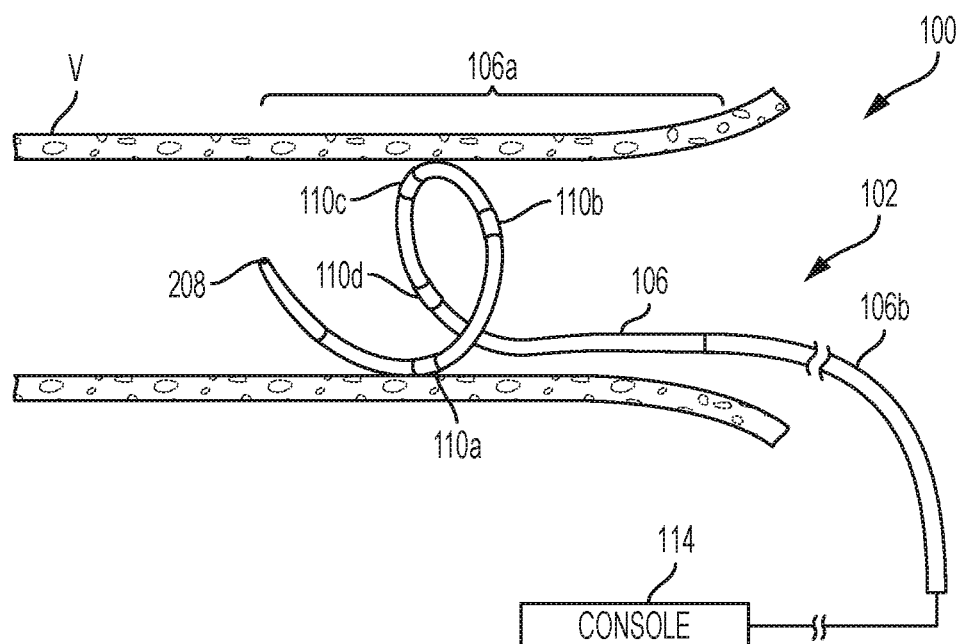

FIG. 1 is a partially schematic illustration of a therapeutic neuromodulation system 100 ("system 100") configured in accordance with an embodiment of the present technology. In the illustrated embodiment, the system 100 includes a neuromodulation catheter 102, a console 114, and a cable 105 extending therebetween. In general, the console 114 is configured to control operation of the neuromodulation catheter 102 for performing neuromodulation therapy (e.g., renal denervation therapy). FIGS. 2A-2C are partially schematic side views of a portion of the system 100 showing the neuromodulation catheter 102 in different arrangements while positioned at a target site within a blood vessel V (e.g., a renal artery) of a human patient.

Referring to FIGS. 1-2C together, the neuromodulation catheter 102 can include an elongated shaft 106 having (i) a distal portion 106a including a plurality of electrodes 110 and configured to be intravascularly positioned at the target site within the blood vessel V, and (ii) a proximal portion 106b extending outside of the patient to a handle 111 or other features that allow an operator to manipulate the distal portion 106a of the elongated shaft 106. In some embodiments, the elongated shaft 106 can be 2, 3, 4, 5, 6, or 7 French or another suitable size. The neuromodulation catheter 102 is configured to perform neuromodulation therapy at the target site to, for example, ablate nerves proximate the wall of the blood vessel V. As discussed in greater detail below, the neuromodulation catheter 102 is further configured to detect one or more measurements related to a blood flow rate through the blood vessel V before, during, and/or after neuromodulation therapy to assess the likely efficacy of delivered neuromodulation energy.

Referring to FIG. 2A, in some embodiments, the system 100 can include a guidewire 201 and the neuromodulation catheter 102 can be advanced over the guidewire 201 to the target site within the blood vessel V. More specifically, as shown in FIG. 2B, the elongated shaft 106 of the neuromodulation catheter 102 is configured to be slidably delivered over the guidewire 201. In other embodiments, the neuromodulation catheter 102 can be configured for delivery to the target site via other methods (e.g., via a guide catheter, via sheath retraction, etc.). The guidewire 201 includes a distal portion 203a configured to be positioned at the target site within the blood vessel V and a proximal portion (not visible) that extends outside of the patient to the handle 111 (FIG. 1) or other feature(s) that allow an operator to manipulate the distal portion 203a to the desired position/orientation. Additionally, the guidewire 201 can have a uniform stiffness along its length or can have a stiffness that varies along its length. In other embodiments, the guidewire 201 may comprise other suitable components and/or configurations.

As shown in FIGS. 2B and 2C, the neuromodulation catheter 102 is transformable between (i) a first state or arrangement in which the distal portion 106a of the elongated shaft 106 is at least generally straight and in a low-profile delivery arrangement (FIG. 2B), and (ii) a second (e.g., deployed, expanded, etc.) state or arrangement in which the distal portion 106a is transformed or otherwise expanded to a spiral/helical shape (FIG. 2C). Referring to FIGS. 2B and 2C together, the neuromodulation catheter 102 includes a plurality of energy delivery elements, such as the electrodes 110, spaced along the distal portion 106a of the elongated shaft 106 and a distal tip 208 (e.g., an atraumatic tip). In the illustrated embodiment, the neuromodulation catheter 102 includes four electrodes 110 (identified individually as first through fourth electrodes 110a-110d, respectively). In other embodiments, however, the neuromodulation catheter 102 may include one, two, three, or more than four electrodes 110, and/or may include different energy delivery elements.

The electrodes 110 are configured to deliver neuromodulation energy to the target site to modulate or ablate nerves (e.g., renal nerves) proximate to the target site. The electrodes 110 are also configured to detect a vessel impedance, such as an impedance between two or more of the electrodes 110 or an impedance between any one of the electrodes 110 and a suitable reference electrode (e.g., a ground patch) that may be internal or external to the patient. In other embodiments, the neuromodulation catheter 102 can include electrodes, transducers, or other elements to deliver energy to modulate nerves using other suitable neuromodulation modalities, such as pulsed electrical energy, microwave energy, optical energy, ultrasound energy (e.g., intravascularly delivered ultrasound and/or high-intensity focused ultrasound (HIFU)), direct heat energy, radiation (e.g., infrared, visible, and/or gamma radiation), and/or other suitable types of energy. In certain embodiments, the neuromodulation catheter 102 may be configured for cryotherapeutic treatment and can apply cryogenic cooling to the vessel V with a refrigerant (e.g., via a balloon catheter that circulates the refrigerant).

The dimensions (e.g., outer diameter and length) of the distal portion 106a of the elongated shaft 106 (e.g., the portion that takes on the spiral/helical shape in the second state illustrated in FIG. 2C) can be selected to accommodate the vessel(s) or other body lumen(s) in which the distal portion 106a is designed to be delivered. For example, when in the second state, the axial length of the distal portion 106a of the elongated shaft 106 may be selected to be no longer than a patient's renal artery (e.g., typically less than 7 cm), and have a diameter that accommodates the inner diameter of a typical renal artery (e.g., about 2-10 mm). In other embodiments, the distal portion 106a of the elongated shaft 106 can have other dimensions depending on the body lumen within which it is configured to be deployed. Regardless of the selected dimensions of the distal portion 106a, in some embodiments, one or more dimensions of the distal portion 106a are known prior to performing a neuromodulation procedure with the neuromodulation catheter 102. In some embodiments, for example, the known dimensions can be used to calculate other (e.g., variable, unknown, non-constant, etc.) dimensions of the distal portion 106a such as a diameter of the distal portion 106a in the spiral/helical second state, a longitudinal distance between the electrodes 110, etc. In further embodiments, the distal portion 106a of the elongated shaft 106 can have other suitable shapes (e.g., semi-circular, curved, straight, etc.), and/or the neuromodulation catheter 102 can include multiple support members configured to carry one or more electrodes 110. The distal portion 106a of the elongated shaft 106 may also be designed to apply a desired outward radial force to a vessel when expanded to the spiral/helical second state to place one or more of the electrodes 110 in contact with the wall of the blood vessel V.

Although the embodiment of the neuromodulation catheter 102 shown in FIGS. 1-2C has a spiral/helically-shaped configuration, in other embodiments, the neuromodulation catheter 102 can have other suitable shapes, sizes, and/or configurations. Other suitable devices and technologies are described in, for example, U.S. Pat. Nos. 8,777,942; 9,084,610; 8,998,894; PCT Application No. PCT/US2011/057754, filed Oct. 25, 2011; and U.S. Pat. No. 8,888,773. All of the foregoing applications are incorporated herein by reference in their entireties. Another non-limiting example of a device includes the Symplicity Spyral™ multielectrode RF ablation catheter.

Referring again to FIG. 1, the console 114 can be configured to control, monitor, supply, and/or otherwise support operation of the neuromodulation catheter 102. For example, as described in greater detail below, the console 114 may be configured to continuously or intermittently monitor vessel impedance. In addition, the console 114 can be configured to provide feedback to an operator before, during, and/or after a treatment procedure via an evaluation/feedback algorithm 116. For example, the console 114 can be configured to provide feedback to the operator about a determined blood flow rate through the blood vessel V and/or a likely efficacy of a neuromodulation procedure performed at the target site.

The console 114 can further be configured to generate a selected form and/or magnitude of energy for delivery to tissue at the treatment site via the electrodes 110, and therefore the console 114 may have different configurations depending on the treatment modality of the neuromodulation catheter 102. For example, when the neuromodulation catheter 102 is configured for electrode-based, heat-element-based, or transducer-based treatment, the console 114 can include an energy generator 170 (shown schematically) configured to generate RF energy (e.g., monopolar and/or bipolar RF energy), pulsed energy, microwave energy, optical energy, ultrasound energy (e.g., intravascularly delivered ultrasound and/or HIFU), direct heat energy, radiation (e.g., infrared, visible, and/or gamma radiation), and/or another suitable type of energy. In this configuration, the console 114 can use the evaluation/feedback algorithms 116 to control energy deliver via the electrodes 110. In selected embodiments, the energy generator 170 can be configured to deliver a monopolar electric field via one or more of the electrodes 110. In such embodiments, a neutral or dispersive electrode 160 may be electrically coupled to the energy generator 170 and attached to the exterior of the patient. When the neuromodulation catheter 102 is configured for cryotherapeutic treatment, the console 114 can include a refrigerant reservoir (not shown) and can be configured to supply the neuromodulation catheter 102 with refrigerant. Similarly, when the neuromodulation catheter 102 is configured for chemical-based treatment (e.g., drug infusion), the console 114 can include a chemical reservoir (not shown) and can be configured to supply the neuromodulation catheter 102 with one or more chemicals.

In some embodiments, the system 100 can further include a controller 104 communicatively coupled to the neuromodulation catheter 102. The controller 104 can be configured to initiate, terminate, and/or adjust operation of one or more components (e.g., the electrodes 110) of the neuromodulation catheter 102 directly and/or via the console 114 and/or via a wired or wireless communication link. In various embodiments, the system 100 can include multiple controllers. In other embodiments, the neuromodulation catheter 102 can be communicatively coupled to a single controller 104. The controller 104 can be integrated with the console 114 or with the handle 111 positioned outside the patient and used to operate the system 100. In other embodiments, the controller 104 can be omitted or have other suitable locations (e.g., along the cable 105). The controller 104 can include computer-implemented instructions to initiate, terminate, and/or adjust operation of one or more components of the neuromodulation catheter 102 directly and/or via another aspect of the system (e.g., the console 114 and/or the handle 111). For example, the controller 104 can further provide instructions to the neuromodulation catheter 102 to apply neuromodulatory energy to the treatment site (e.g., RF energy via the electrodes 110). The controller 104 can be configured to execute an automated control algorithm and/or to receive control instructions from an operator. Further, the controller 104 can include or be linked to the evaluation/feedback algorithm 116 that can provide feedback to an operator before, during, and/or after a treatment procedure via a console, monitor, and/or other user interface.

The system 100 can also include an injector mechanism 180 (shown schematically) configured to deliver an indicator fluid (e.g., an injectate) to the blood vessel V before, during, and/or after a neuromodulation procedure using the neuromodulation catheter 102. In some embodiments, the indicator fluid is a contrast agent for use in an imaging procedure (e.g., to aid an operator in locating or positioning the neuromodulation catheter 102 within the blood vessel V). In other embodiments, the indicator fluid can be a radiolucent fluid such as saline or a mannitol solution. The indicator fluid has a resistivity that is different than a resistivity of the blood within the blood vessel V such that the indicator fluid can cause a transient change in impedance within the blood vessel V. As described in greater detail below, detection of such a transient impedance change can facilitate measurement of the blood flow rate through the blood vessel V.

Figure 4:
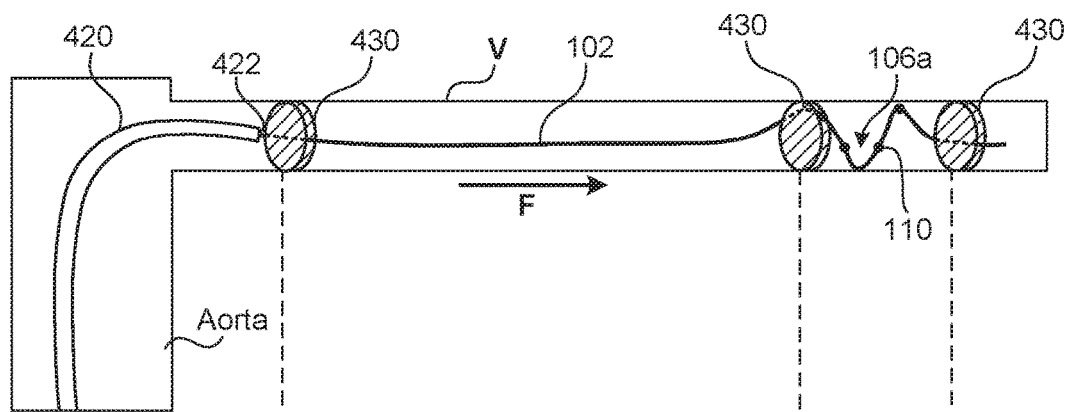
FIG. 4 is a partially schematic side view of the neuromodulation system of FIG. 1 showing the flow of an indicator fluid through a blood vessel of a human patient in accordance with an embodiment of the present technology.

In the embodiment illustrated in FIG. 1, the injector mechanism 180 is fluidly coupled to the neuromodulation catheter 102 (e.g., to the proximal portion 106b of the neuromodulation catheter 102). In such embodiments, the neuromodulation catheter 102 can include one or more ports and/or lumens (not shown) for delivering the indicator fluid into the blood vessel V. In certain embodiments, for example, the neuromodulation catheter 102 can include one or more ports positioned proximal to the distal portion 106a of the neuromodulation catheter 102 for delivering/injecting the indicator fluid proximal to the target site and the distal portion 106a of the neuromodulation catheter 102 (e.g., upstream relative to the flow of blood through the blood vessel V). In other embodiments, the injector mechanism 180 can alternatively or additionally be fluidly coupled to a guide catheter used to deliver the neuromodulation catheter 102 to the target site in the blood vessel V (e.g., as shown in FIG. 4 below). In some such embodiments, the indicator fluid can be delivered from a distal end portion of the guide catheter upstream of the target site and the distal portion 106a of the neuromodulation catheter 102. In some embodiments, the injector mechanism 180 can be an automatic injector configured to deliver a known volume of indicator fluid and/or can be configured to deliver the indicator fluid into the blood vessel V substantially instantaneously and/or as a bolus (e.g., as a fluid plug of substantially constant diameter). In certain embodiments, the controller 104, the console 114, and/or another component of the system 100 can be configured to control the injector mechanism 180 for delivering the indicator fluid.

Figure 3:
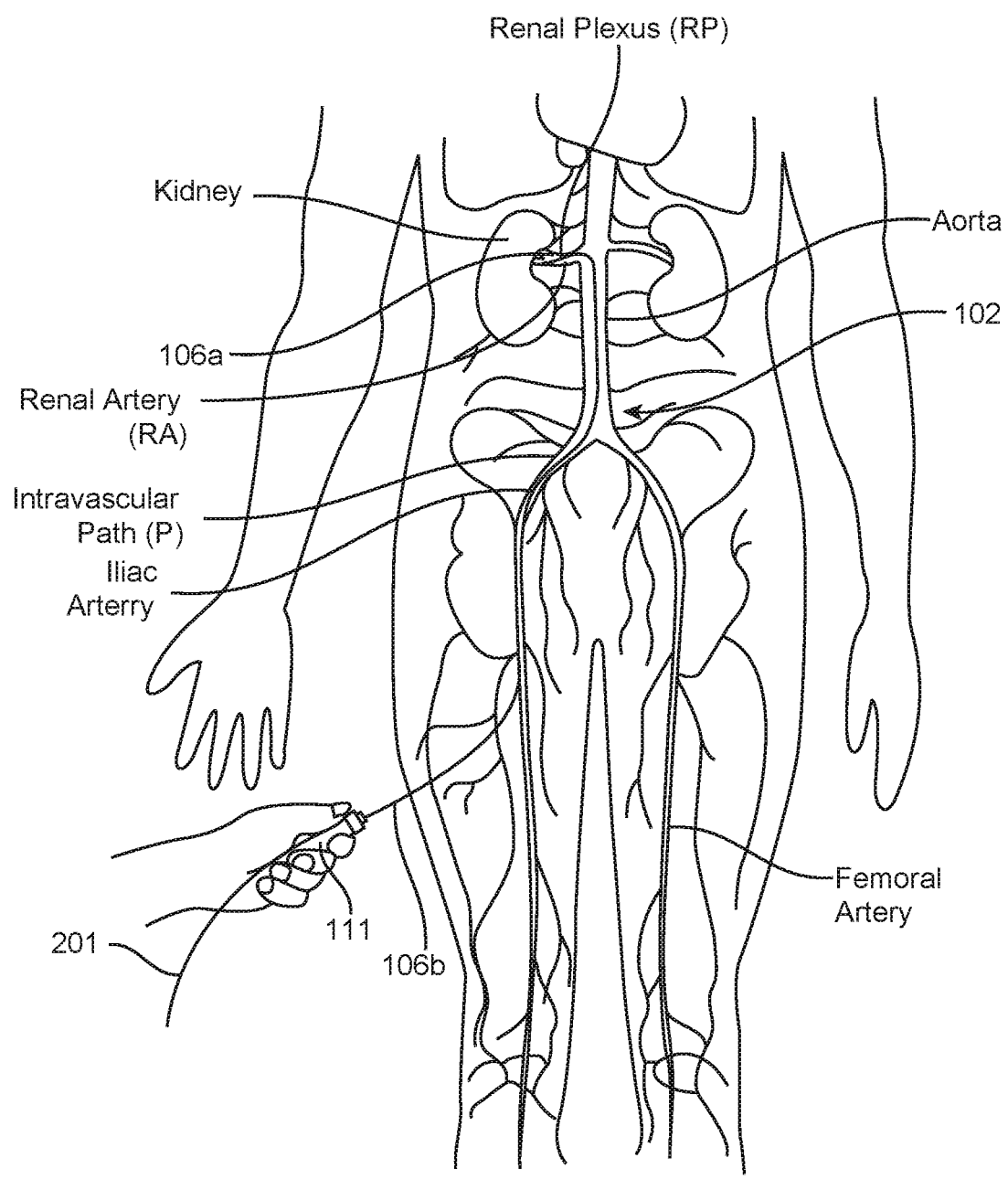
FIG. 3 illustrates modulating renal nerves and/or evaluating neuromodulation therapy with the system of FIG. 1 in accordance with an embodiment of the present technology.

FIG. 3 (with additional reference to FIG. 1-2C) illustrates modulating renal nerves in accordance with an embodiment of the present technology. The neuromodulation catheter 102 provides access to the renal plexus RP through an intravascular path P, such as a percutaneous access site in the femoral (illustrated), brachial, radial, or axillary artery to a targeted treatment site within the blood vessel V (e.g., within a respective renal artery RA). By manipulating the proximal portion 106b of the elongated shaft 106 from outside the intravascular path P, a clinician may advance the elongated shaft 106 through the sometimes tortuous intravascular path P and remotely manipulate the distal portion 106a of the elongated shaft 106. In the embodiment illustrated in FIG. 3, the distal portion 106a of the elongated shaft 106 is delivered intravascularly to the treatment site using the guidewire 201 in an OTW technique. The distal end of the neuromodulation catheter 102 may define a passageway for receiving the guidewire 201 for delivery of the neuromodulation catheter 102 using either OTW or RX techniques. At the treatment site, the guidewire 201 can be at least partially withdrawn or removed, and the distal portion of the neuromodulation catheter 102 can transform or otherwise be moved to a deployed arrangement for recording neural activity and/or delivering energy at the treatment site. In other embodiments, the neuromodulation catheter 102 may be delivered to the treatment site within a guide catheter (e.g., a guide sheath) with or without using the guidewire 201. When the neuromodulation catheter 102 is at the target site, the guide catheter may be at least partially withdrawn or retracted and the distal portion 106a of the neuromodulation catheter 102 can be transformed into the deployed arrangement. In still other embodiments, the elongated shaft 106 may be steerable itself such that the neuromodulation catheter 102 may be delivered to the treatment site without the aid of the guidewire 201 and/or a guide catheter.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation catheter 102. For example, a fluoroscopy system (e.g., including a flat-panel detector, x-ray, or c-arm) can be rotated to accurately visualize and identify the target treatment site. As described in detail above, in some embodiments, the injector mechanism 180 can be used to inject a fluoroscopic contrast agent for use in imaging. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation catheter 102. Further, in some embodiments, image guidance components (e.g., IVUS, OCT) may be integrated with the neuromodulation catheter 102 and/or run in parallel with the neuromodulation catheter 102 to provide image guidance during positioning of the neuromodulation catheter 102. For example, image guidance components (e.g., IVUS or OCT) can be coupled to the neuromodulation catheter 102 to provide three-dimensional images of the vasculature proximate the target site to facilitate positioning or deploying the multi-electrode assembly within the target renal blood vessel.

Energy from the electrodes 110 and/or other energy delivery elements may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

II. METHODS FOR ESTIMATING BLOOD FLOW AND ASSESSING THE EFFICACY OF NEUROMODULATION THERAPY

As described above, it is expected that successful or effective neuromodulation therapy (e.g., when nerves are ablated to a desired degree) causes vasodilation of the vascular bed in the ablated blood vessel. Accordingly, it may be advantageous to detect one or more measurements related to the blood flow rate through a targeted blood vessel to determine an increase—or lack thereof—in the blood flow rate as a result of neuromodulation therapy and, correlatively, an efficacy of the neuromodulation therapy. In general, as detailed below, the system 100 of the present technology is configured to detect one or more measurements related to the blood flow rate through a blood vessel before, during, and/or after delivery of neuromodulation energy to that blood vessel. More specifically, the system 100 is configured to detect and/or measure a change in vessel impedance resulting from flow of an injector fluid (e.g., a contrast agent, saline solution, mannitol solution, etc., having a resistivity different than that of blood) past the distal portion 106a of the neuromodulation catheter 102.

Figure 5:
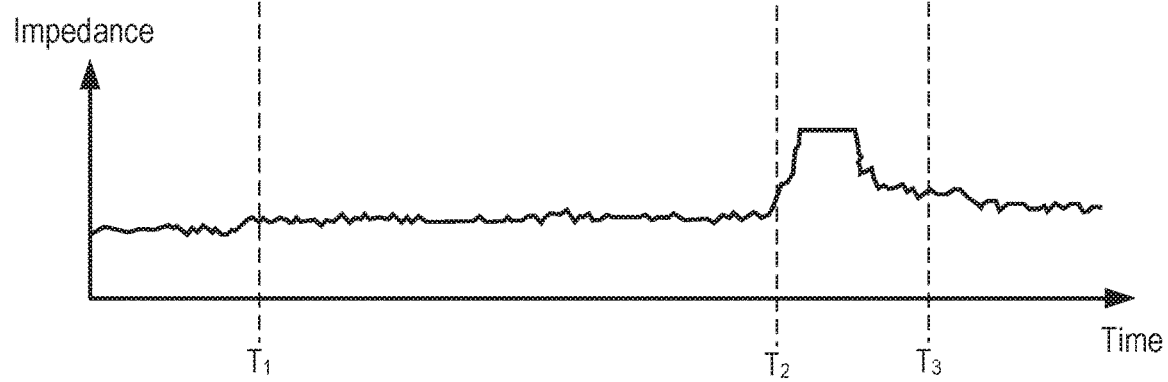
FIG. 5 is a graph illustrating an impedance curve or profile detected by the neuromodulation system of FIG. 1 in accordance with an embodiment of the present technology.

FIG. 4, for example, is a partially schematic side view of the neuromodulation catheter 102 of FIGS. 1-2C deployed at the target site within the blood vessel V from a guide catheter 420 in accordance with an embodiment of the present technology. FIG. 4 also illustrates the movement (e.g., flow) of an indicator fluid 430 through the blood vessel V after injection from a distal end portion 422 of the guide catheter 420. In other embodiments, as described in detail above, the indicator fluid 430 can be delivered from one or more ports in the neuromodulation catheter 102 and/or via other suitable means. FIG. 5 is a graph illustrating an impedance curve or profile of the resulting impedance of the blood vessel V over time. The vessel impedance can be detected and/or measured using one or more of the electrodes 110 of the neuromodulation catheter 102. In some embodiments, the vessel impedance can be measured using (i) a bipolar technique that measures the impedance between any pair of electrodes 110 or between any individual electrode 110 and a reference electrode that is external or internal to the patient (e.g., the dispersive electrode 160 (FIG. 1)), (ii) a quadripolar technique in which the two outer ones of the electrodes 110 (e.g., the most proximally and distally positioned ones of the electrodes 110) are used to drive a constant electrical current while the two inner ones of the electrodes 110 are used to measure the resultant voltage and hence impedance, (iii) or any combination thereof. In some embodiments, a quadripolar technique can provide a more homogenous electric field across the cross-sectional area of the blood vessel V, resulting in a more accurate measure of impedance.

Referring first to FIG. 4, the indicator fluid 430 is injected (e.g., delivered) into the blood vessel V upstream of the distal portion 106a of the neuromodulation catheter 102 and the target site at a time $T_1$. In the illustrated embodiment, the indicator fluid 430 is injected as a bolus having a cross-sectional dimension that substantially matches that of the blood vessel V. Blood flow in the direction F causes the injected mass of indicator fluid 430 to flow toward and past the distal portion 106a of the neuromodulation catheter 102 and the electrodes 110 thereon. Referring to FIG. 5, the vessel impedance is generally constant from the time $T_1$ until a time $T_2$ at which the indicator fluid 430 begins to pass through the blood vessel V proximate to the electrodes 110, thereby causing a transient change (e.g., a spike) in the vessel impedance. The transient change in impedance is the result of the indicator fluid 430 having a resistivity that is different than the blood in the blood vessel V (e.g., is hyper- or hypo-resistive compared to the blood). As the indicator fluid 430 passes downstream past the electrodes 110, the vessel impedance begins to return to a baseline value. For example, when substantially all of the indicator fluid 430 has passed the electrodes 110 (e.g., at a time $T_3$), the vessel impedance has generally the same baseline value as before the time $T_2$.

The detected transient change in vessel impedance can be used to estimate the blood flow rate through the blood vessel V. For example, the transient change in impedance can be modeled as an indicator-dilution curve. Accordingly, the blood flow rate can be estimated using the standard indicator-dilution equation (simplified into summation rather than integral form for convenient digital calculation):

$$F_v = \frac{R_i A_v}{\sum R(t) \Delta t} \quad (1)$$

The indicator-dilution equation (1) provides that the blood flow rate $F_v$ through the blood vessel V is proportional to the impedance $R_i$ of the indicator fluid 430, the cross-sectional area $A_v$ of the blood vessel V, and the transient change in vessel impedance $\tau R(f) \Delta t$. The impedance $R_i$ of the indicator fluid 430 can be estimated using the cylindrical equation:

$$R_i = \frac{\rho_i L_i}{A_v} = \frac{\rho_i L_i^2}{V_i} \quad (2)$$

The cylindrical equation (2) provides that the impedance $R_i$ of a cylinder (e.g., a fluid column) of the indicator fluid 430 having a relatively constant diameter and a constant resistivity $\rho_i$ is determined by the cross-sectional area $A_v$ of the blood vessel V and the effective length $L_i$ of the cylinder of the indicator fluid 430 in the blood vessel V, which is determined by the volume $V_i$ of the indicator fluid 430 injected into the blood vessel V and the cross-sectional area $A_v$ of the blood vessel V (i.e., $L_i = V_i / A_v$). The cross-sectional area $A_v$ can be estimated from a fluoroscopic image of the blood vessel V, another noninvasive imaging technique, or other techniques known in the art before, during, and/or after a neuromodulation procedure. The resistivity $\rho_i$ and volume $V_i$ of the indicator fluid 430 can be known values that are selectable by the operator of the system 100, or can be directly measured or estimated before, during, and/or after the neuromodulation procedure. Substituting equation (2) into equation (1) yields:

$$F_v = \frac{\rho_i L_i^2}{\sum R(t) \Delta t} \quad (3)$$

The transient change in vessel impedance $\Sigma R(t)\Delta t$ can be calculated by summing or integrating the measured indicator-dilution curve. For example, the console 114, the controller 104, and/or another component of the system 100 can be configured to sum or integrate the measured indicator-dilution curve from the time $T_2$ (e.g., when the indicator fluid 430 begins to pass proximate to the distal portion 106a of the neuromodulation catheter 102) to the time $T_3$ (e.g., when the indicator fluid 430 has passed substantially downstream of distal portion 106a)—or over a wider time interval—to determine the transient change in vessel impedance $\Sigma R(t)\Delta t$ and thus the flow rate $F_v$ through the blood vessel V.

In some embodiments, the equation (3) could require correction due to potential sources of error including, for example, (i) current leakage into the surrounding tissue of the blood vessel V during impedance measurements made using the electrodes 110, (ii) non-homogeneity of the impedance field across the cross-sectional area $A_v$ of the blood vessel V, and/or (iii) non-uniformity of the indicator fluid 430 such that the indicator fluid 430 does not substantially resemble a cylinder as it flows through the blood vessel V (e.g., caused by non-instantaneous injection of the indicator fluid). Accordingly, a corrected version of equation (3) could be:

$$F_v = k \left[ \frac{\rho_i L_i^2}{\sum R(t) \Delta t} \right] - F_o \quad (4)$$

The equation (4) contains an offset $F_o$ and a gain term k that can correct for potential sources of error in the equation (3). In some embodiments, the values of $F_o$ and k can be determined empirically by comparing the calculated flow rate $F_v$ from equation (3) to a flow rate measured directly—for example, a flow rate measured using a flow wire, a transit time flow probe, or other device in a series of human and/or animal experiments.

Figure 6:
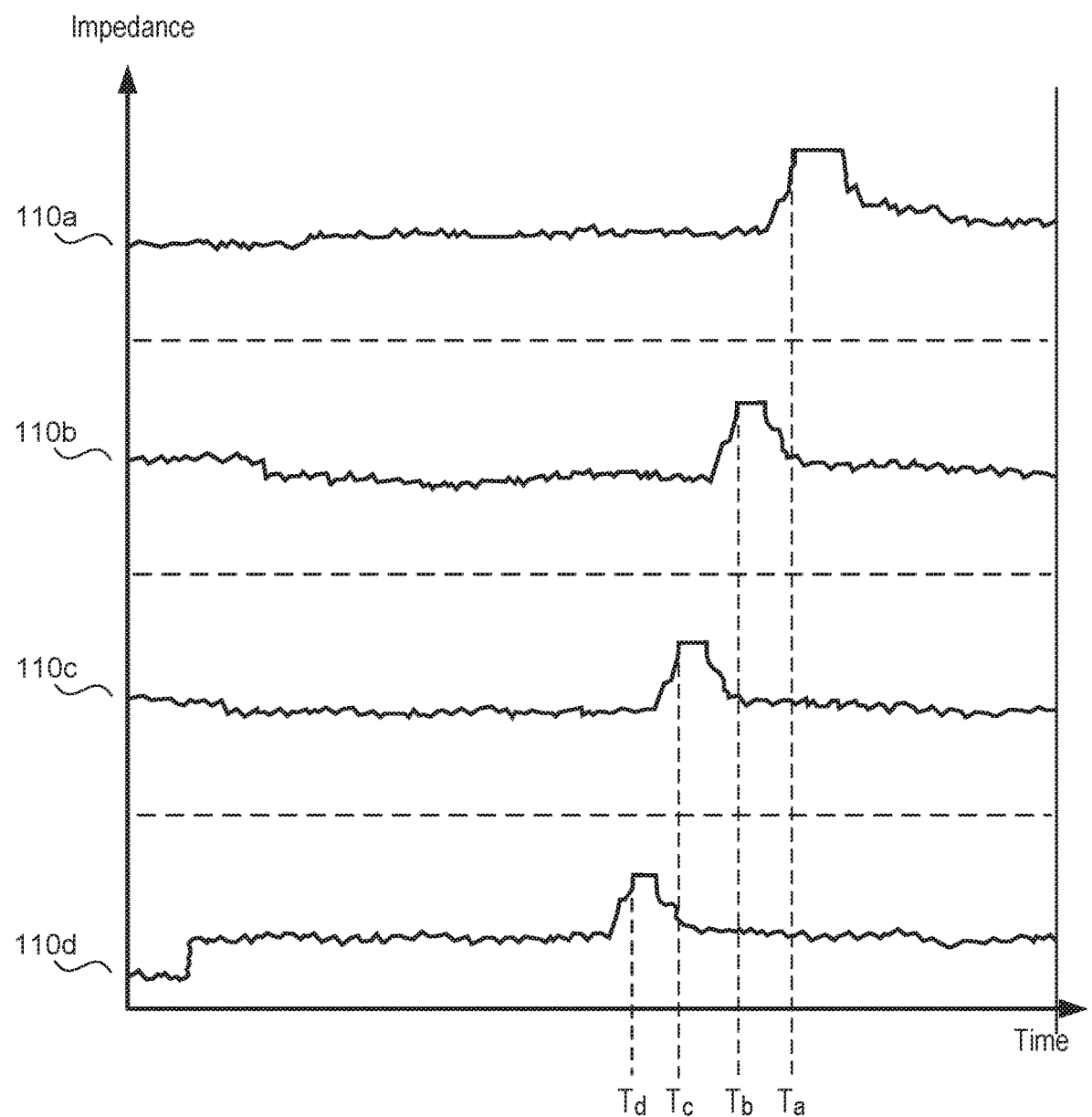
FIG. 6 is a graph illustrating multiple impedance curves or profiles detected by the neuromodulation system of FIG. 1 in accordance with an embodiment of the present technology.

In some embodiments, the flow rate $F_v$ can be estimated based on at least one time difference between detecting the transient change in impedance at two or more electrodes of the neuromodulation catheter 102. That is, for example, the flow rate $F_v$ can be determined based on a time lag of arrival of the bolus of indicator fluid 430 between at least one of the electrodes 110 and another, more distal (e.g., downstream) one of the electrodes 110. FIG. 6, for example, is a graph illustrating the vessel impedance, measured over time, at each of the four electrodes 110. In other embodiments, the neuromodulation catheter 102 can include one or more electrodes in addition to the ablation electrodes 110 that can be used to detect the arrival of the indicator fluid 430 (e.g., one or more electrodes positioned proximally or distally of the electrodes 110 and that need not be configured to deliver neuromodulation energy). In some embodiments, the impedance measurements via the electrodes 110 (or additional electrodes on the neuromodulation catheter 102) can be unipolar measurements made with reference to a ground patch (e.g., the dispersive electrode 160).

Referring to FIG. 6, the transient change in vessel impedance (i.e., the "spike" in impedance) is detected first at the most proximal electrode 110d and lastly at the most distal electrode 110a, as the indicator fluid 430 flows distally past the distal portion 106a of the neuromodulation catheter 102. In the illustrated embodiment, the indicator fluid 430 is defined as arriving at each of the electrodes 110a-110d at times $T_a$-$T_d$, respectively, when the peak (e.g., plateau) of the impedance curve begins. Although the vessel impedance is shown having a truncated peak in FIG. 6, the vessel impedance can resemble a smooth curve where the impedance sampling resolution is greater. In other embodiments, the time of arrival can be defined differently (e.g., at the beginning of the impedance curve, at the end of the impedance curve, etc.). The system 100 (e.g., the console 114 and/or the controller 104) can determine a time difference $\Delta t$ of arrival of the indicator fluid 430 between any one or more pairs of the electrodes 110 (e.g., differences between the times $T_a$-$T_d$) that can be used to estimate the flow rate $F_v$. More specifically, the pulse wave velocity $V_v$ of the blood in the blood vessel V can be determined based on the measured time difference $\Delta t$ and a longitudinal distance D between the particular ones of the electrodes 110 used to calculate the time difference $\Delta t$, by the equation:

$$V_v = \frac{\Delta t}{D} \quad (5)$$

In some embodiments, the time difference $\Delta t$ can be measured with the distal portion 106a of the neuromodulation catheter 102 in the generally straight low-profile delivery arrangement (FIG. 2B). In such embodiments, the distance D is known. In other embodiments, the time difference $\Delta t$ can be measured with the distal portion 106a of the neuromodulation catheter 102 in the second (expanded) state (FIG. 2C). In such embodiments, the distance D can be estimated based on, for example, the cross-sectional area $A_v$ of the blood vessel V and a known angle of rotation of the distal portion 106a of the neuromodulation catheter 102 when the neuromodulation catheter 102 is in the second state and apposed against the wall of the blood vessel V. The flow rate $F_v$ can be determined simply by dividing the velocity $V_v$ by the cross-sectional area $A_v$ of the blood vessel V:

$$F_v = \frac{V_v}{A_v} \quad (6)$$

As set forth above, the cross-sectional area $A_v$ can be estimated from a fluoroscopic image of the blood vessel V, another noninvasive imaging technique, and/or other techniques known in the art. Once the flow rate $F_v$ has been estimated using any one or combination of the techniques described in detail above, the vascular $Z_v$ resistance of the blood vessel V can be determined by dividing the mean pressure Pv of the blood vessel V by the calculated flow rate $F_v$:

$$Z_v = \frac{P_v}{F_v} \quad (7)$$

The mean pressure $P_v$ of the blood vessel V can be measured directly from within the blood vessel V using a fluid filled sensor, high fidelity micromanometer, or another suitable device. In other embodiments, the mean pressure Pv could be estimated based on measured aortic, iliac, or femoral pressure, or estimated noninvasively based on a standard cuff measurement. In some embodiments, the vascular resistance $Z_v$ provides a more useful measurement for comparing flow rates before and after neuromodulation energy is delivered to the blood vessel V, as it controls for differences in the flow rate $F_v$ that may be caused by differing mean pressures within the blood vessel V.

Figure 7:
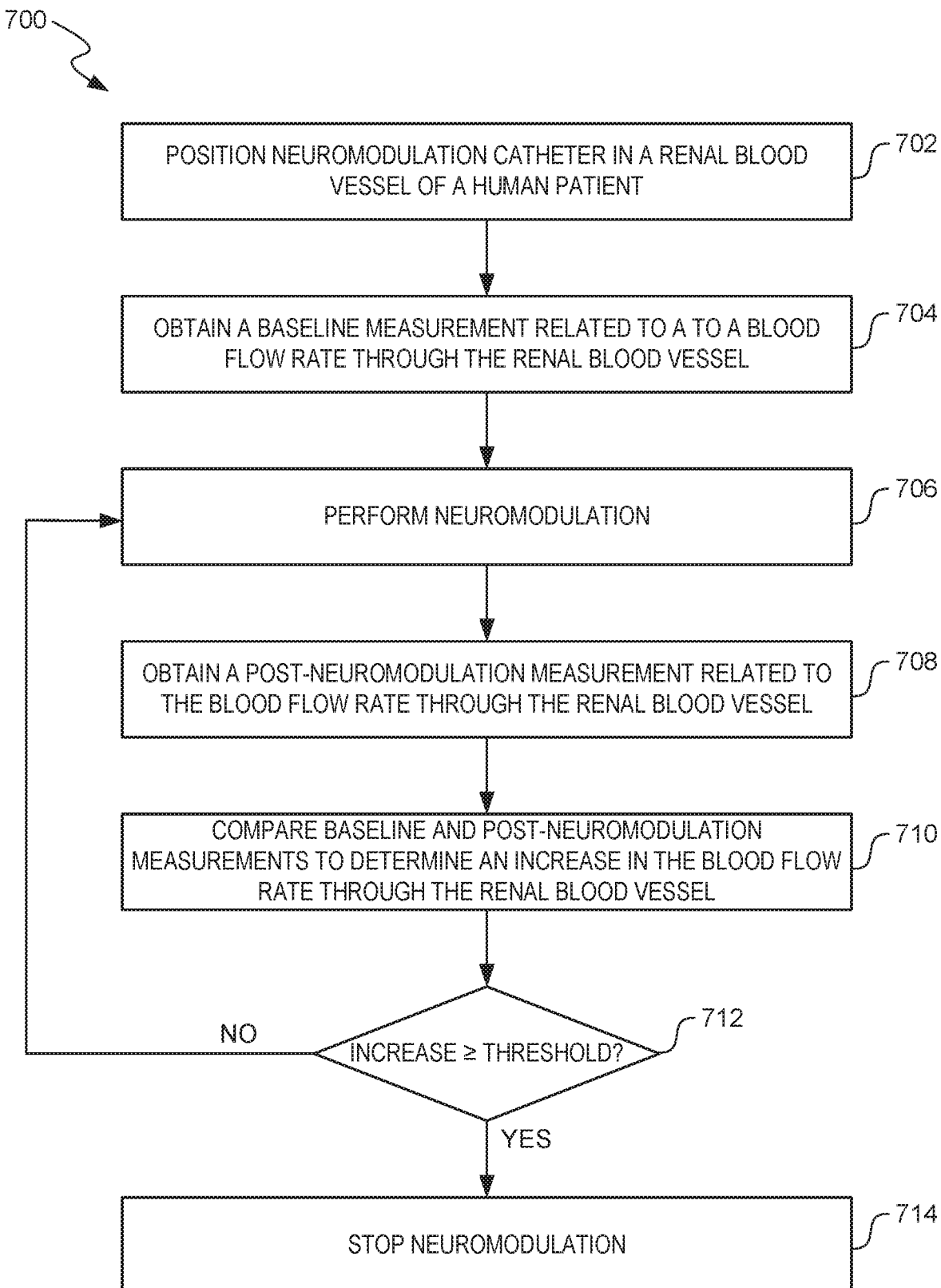
FIG. 7 is a flow diagram of a process or method for assessing the efficacy of neuromodulation therapy in accordance with embodiments of the present technology.

FIG. 7 is a flow diagram of a method or process 700 for evaluating the efficacy of neuromodulation therapy in accordance with embodiments of the present technology. The method 700 can be implemented using the system 100 described in detail above with reference to FIGS. 1A-6 and/or using other suitable systems for evaluating the efficacy of neuromodulation therapy. For example, the neuromodulation catheter 102, the controller 104, and/or the console 114 can be used to perform the various steps of the method 700. Accordingly, for sake of illustration, some features of the method 700 will be described in the context of the embodiments shown in FIGS. 1A-6.

Beginning at block 702, the method 700 includes positioning the neuromodulation catheter 102 at a target site within the blood vessel V of the human patient. In some embodiments, positioning the neuromodulation catheter 102 includes (i) positioning the guidewire 201 along a portion of the blood vessel V proximate the target site (FIG. 2A), (ii) advancing the neuromodulation catheter 102 over the guidewire 201 to the target site (FIG. 2C), and (iii) transforming or otherwise expanding the distal portion of the neuromodulation catheter 102 to the spiral/helical shape in which the electrodes 110 contact the wall of the blood vessel V (FIG. 2C). In some embodiments, the neuromodulation catheter 102 can be delivered to the target site in the blood vessel V through a guide catheter such as the guide catheter 420 (FIG. 4), with or without the guidewire 201.

At block 704, the method 700 includes obtaining at least one baseline measurement related to a blood flow rate through the blood vessel V. In some embodiments, the baseline measurement is estimated by injecting a first portion of the indicator fluid 430 into the blood vessel V and detecting a change in vessel impedance as a result of the first portion flowing past the distal portion 106a of the neuromodulation catheter 102, as described in detail above. For example, the console 114 and/or the controller 104 can detect a time difference between arrival of the first portion of the indicator fluid 430 at two or more of the electrodes 110, and/or can sum the transient change in vessel impedance based on measurements from one or more of the electrodes 110. The baseline measurement can be (i) simply the determined time difference and/or transient change in vessel impedance (e.g., a measurement related to the blood flow rate), (ii) the actually determined blood flow rate, (iii) the renal resistance calculated from the blood flow rate, (iv) or another related value. Moreover, the baseline measurement can be a single measurement or a composite or average of several different measurements. For example, the baseline measurement can be an average or composite of several different measurement techniques and/or measurements derived from different ones or combinations of the electrodes 110. In some embodiments, the obtained baseline measurement can be communicated to and stored in the memory of the controller 104, the console 114, and/or another component of the system 100.

At block 706, the method 700 includes performing neuromodulation therapy with the neuromodulation catheter 102 at the target site in the blood vessel V to, for example, ablate nerves proximate to the wall of the blood vessel V. For example, the method 700 can include applying RF energy (e.g., via the electrodes 110), pulsed electrical energy, microwave energy, optical energy, ultrasound energy (e.g., intravascularly delivered ultrasound and/or HIFU), direct heat energy, radiation, cryogenic cooling, chemical-based treatment, and/or another suitable type of neuromodulation energy.

At block 708, the method 700 includes determining at least one post-neuromodulation measurement related to the blood flow rate through the blood vessel V. The post-neuromodulation measurement can be estimated in generally the same manner as the baseline measurement described above with reference to block 704. For example, a second portion of the indicator fluid 430 can be injected into the blood vessel V and the system 100 can detect the resulting change in vessel impedance via the neuromodulation catheter 102. The post-modulation measurement can include a single measurement or a composite or average of several different measurements. In some embodiments, the obtained post-modulation measurement is communicated to and/or stored in the memory of the controller 104, the console 114, and/or another component of the system 100.

At block 710, the method 700 includes comparing the obtained baseline measurement (block 704) and post-neuromodulation measurement (block 708) to determine an increase in the blood flow rate through the blood vessel V and/or a decrease in the vascular resistance of the blood vessel V, if any, as a result of the neuromodulation therapy (block 706). In some embodiments, the comparison can be performed automatically by the controller 104, the console 114, and/or another component of the system 100. In certain embodiments, the determined increase in the blood flow rate and/or decrease in the vascular resistance can be an absolute increase or decrease. In other embodiments, the determined increase or decrease is a percentage increase or decrease. For example, a baseline measurement of the transient change in vessel impedance (after injection of a portion of the indicator fluid 430) can be simply compared to a post-neuromodulation measurement of the transient change in vessel impedance (after injection of another portion of the indicator fluid 430). One advantage of a percentage change approach is that at least some of the additional measurements or values needed for calculating the absolute flow rate (e.g., the effective length $L_f$, the cross-sectional area $A_v$, etc.) need not be known so long as they are constant between measurements. Similarly, substantially constant sources of error (e.g., the offset $F_o$) need not be estimated. In some embodiments, the determined increase in blood flow rate and/or decrease in vascular resistance can be used to assess the efficacy of the performed modulation therapy by, for example, correlating the percentage change to expected results (e.g., an expected amount of renal nerve destruction, an expected drop in blood pressure at a certain point after a renal denervation procedure, etc.).

In certain embodiments, at block 712, the determined increase in blood flow rate and/or decrease in vascular resistance can be compared to a threshold value associated with effective neuromodulation. The threshold value, for example, can be (i) equivalent to a percentage change (e.g., a 5% change, a 10% change, a 15% change, a 20% change, a 50% change, etc.) in the blood flow rate and/or vascular resistance, or (ii) a predefined absolute increase in flow rate and/or decrease in vascular resistance. If the change is greater than or equal to the predetermined threshold, the operator can elect to stop neuromodulation therapy at block 714. In some embodiments, the operator can then remove the neuromodulation catheter 102 from the blood vessel V, or reposition the neuromodulation catheter 102 to a different target site for delivering additional neuromodulation energy to the different target site.

If the change is less than the predetermined threshold, the operator can elect to apply one or more additional rounds of neuromodulation therapy to the treatment site using the same energy level or a higher energy level. After the additional neuromodulation therapy, the operator can subsequently detect the change, if any, in the blood flow rate and/or vascular resistance as described in detail above. In such situations, the controller 104, the console 114, and/or another component of the system 100 can be configured to store the post-neuromodulation measurement (block 708) as the new baseline measurement. In certain embodiments, the operator can alternatively or additionally reposition the distal portion 106a of the neuromodulation catheter 102 along the blood vessel V to apply neuromodulation energy to a different target site.

As described above, research suggests that there is a correlation between the increase in renal blood flow following a renal denervation procedure and the efficacy of the procedure (e.g., a desired amount of renal nerve destruction, an ultimate drop in blood pressure, etc.). Accordingly, comparing measurements related to the renal blood flow rate before and after neuromodulation is expected to provide one indication of whether a neuromodulation procedure is successful. Accordingly, the system 100 is expected to provide practitioners with a rapid indication of whether a successful neuromodulation treatment has occurred. Thus, practitioners do not need to wait until after the procedure—in some instances for months—to determine whether the treatment was effective. Moreover, any additional neuromodulation energy applications necessary to effectuate neuromodulation therapy can be performed while the neuromodulation catheter 102 is still within the blood vessel V. Accordingly, the system 100 can facilitate efficient and effective neuromodulation treatments.

III. RENAL NEUROMODULATION

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic over activity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment sites during a treatment procedure. The treatment site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a treatment site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., HIFU energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., HIFU energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, optical coherence tomography, or another suitable imaging modality). For example, imaging can be used to identify an anatomical position of a treatment location (e.g., as a set of coordinates relative to a reference point). The coordinates can then be entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

IV. RELATED ANATOMY AND PHYSIOLOGY

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 8:
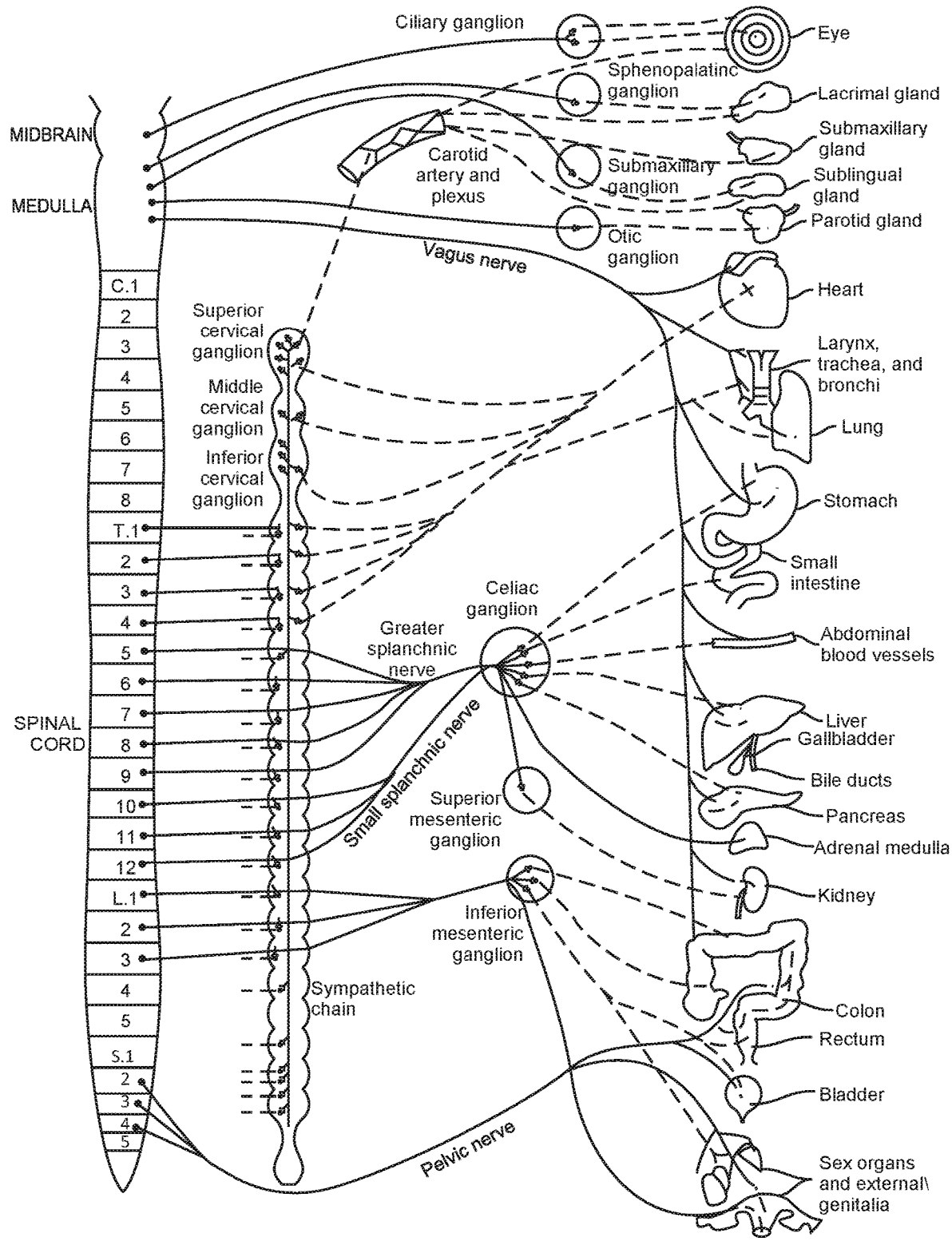
FIG. 8 is a conceptual illustration of the sympathetic nervous system (SNS) and how the brain communicates with the body via the SNS.

As shown in FIG. 8, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 9:
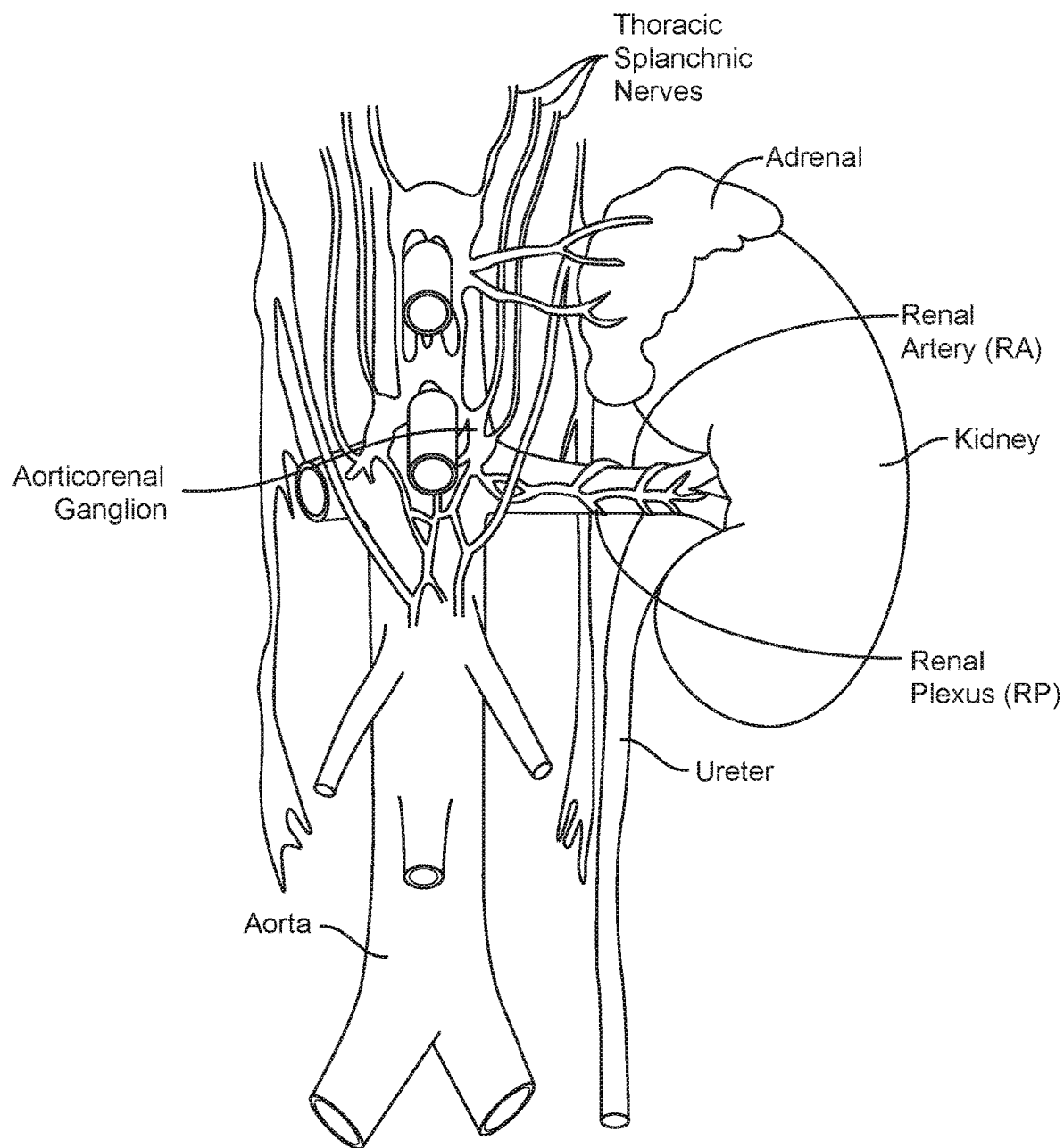
FIG. 9 is an enlarged anatomic view of nerves innervating a left kidney to form the renal plexus surrounding the left renal artery.

As FIG. 9 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 10:
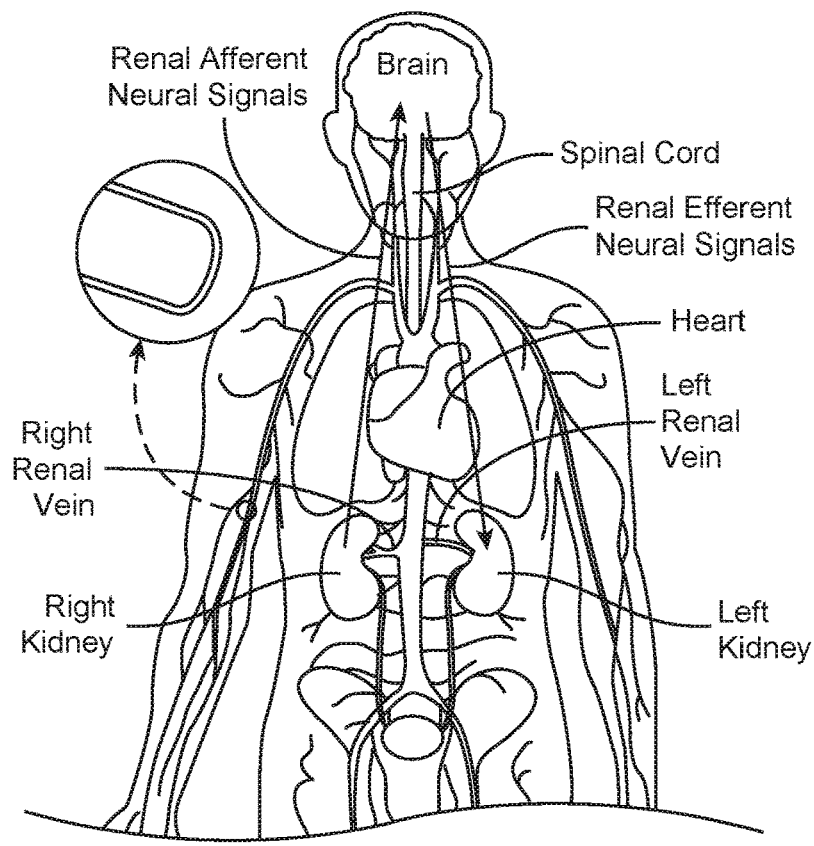
FIGS. 10 and 11 are anatomic and conceptual views, respectively, of a human body depicting neural efferent and afferent communication between the brain and kidneys.
Figure 11:
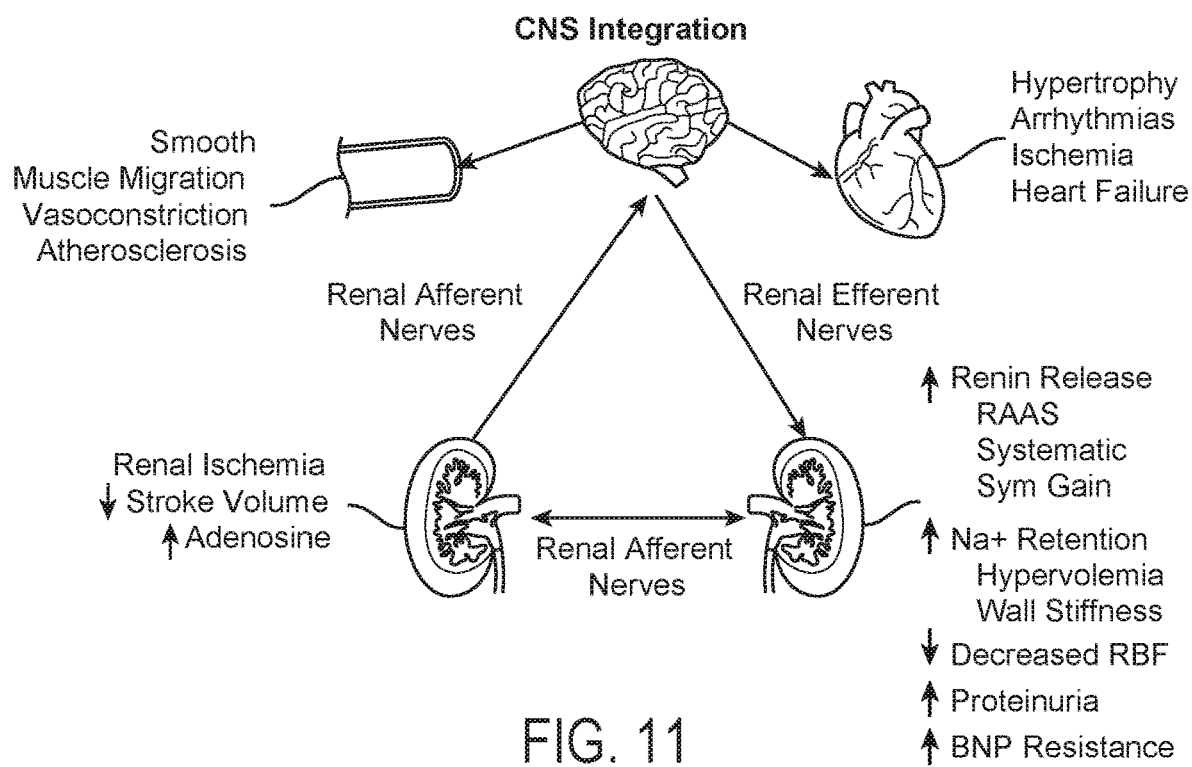

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 10 and 11, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 8. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 12:
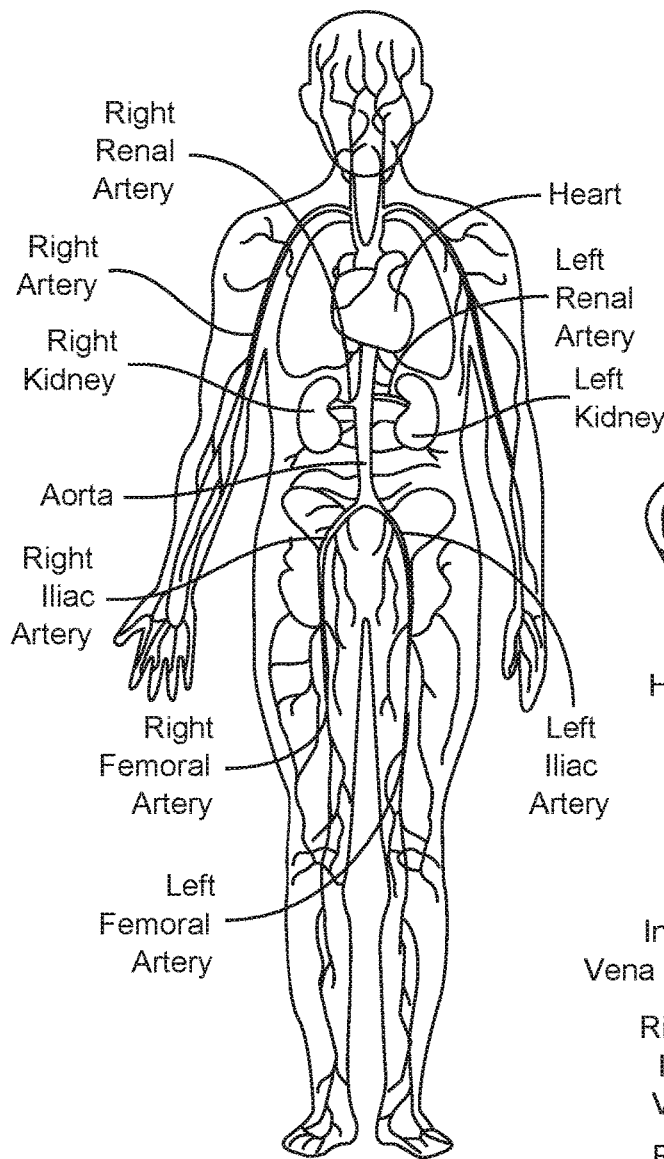
FIGS. 12 and 13 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 12 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 13:
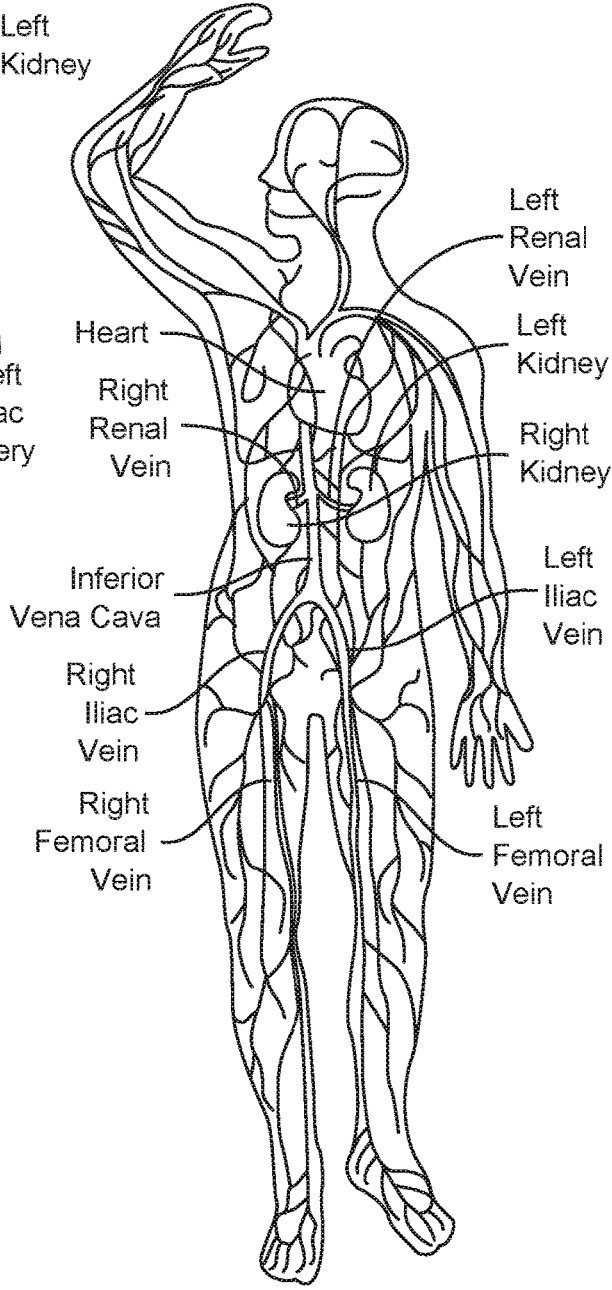

As FIG. 13 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

V. CONCLUSION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:
1. A method comprising:
   positioning a catheter including one or more electrodes at a target site within a blood vessel of a patient;
   delivering neuromodulation energy at the target site via at least one electrode of the one or more electrodes of the catheter;
   introducing a bolus of an indicator fluid into the blood vessel upstream of the target site relative to a direction of blood flow in the blood vessel, the bolus having a known volume;
   obtaining a measurement related to a blood flow rate through the blood vessel via the catheter, wherein obtaining the measurement related to the blood flow rate includes:
      determining a transient change in an impedance in the blood vessel resulting from the bolus of the indicator fluid;
      determining the measurement related to the blood flow rate based on the transient change in the impedance and the known volume; and
      correcting the measurement related to the blood flow rate for at least one of a current leakage into surrounding tissue of the blood vessel or a non-homogeneity of an impedance field across a cross-sectional area of the blood vessel, wherein correcting the measurement is based on a flow rate offset and a flow rate gain term;
   comparing the measurement to a baseline measurement related to the blood flow rate through the blood vessel; and
   assessing efficacy of neuromodulation therapy based, at least in part, on the comparison.
2. The method of claim 1, wherein determining the transient change in the impedance in the blood vessel comprises detecting the impedance via at least one electrode of the one or more electrodes.

3. The method of claim 2, wherein obtaining the measurement related to the blood flow rate includes summing the transient change in impedance over time.

4. The method of claim 2, wherein the indicator fluid has a resistivity different than a resistivity of the blood in the blood vessel.

5. The method of claim 1, wherein determining the transient change in the impedance comprises:
    determining an indicator-dilution curve from a first time corresponding to when the indicator fluid begins to flow past the one or more electrodes to a second time corresponding to when the indicator fluid has passed downstream of the one or more electrodes; and
    integrating the indicator-dilution curve.

6. The method of claim 1, further comprising obtaining the baseline measurement related to the blood flow rate via the catheter before delivering the neuromodulation energy at the target site.

7. The method of claim 6, wherein the bolus includes a first bolus having a first known volume, and wherein obtaining the baseline measurement comprises, before delivering the neuromodulation energy at the target site:
    introducing a second bolus of the indicator fluid into the blood vessel upstream of the target site relative to the direction of blood flow in the blood vessel, the second bolus having a second known volume;
    determining a transient change in the impedance in the blood vessel resulting from the second bolus of the indicator fluid via at least one electrode of the one or more electrodes; and
    determining the baseline measurement based on the transient change in the impedance resulting from the second bolus and the second known volume.

8. The method of claim 1, wherein comparing the measurement related to the blood flow rate to the baseline measurement includes determining at least one of an increase in the blood flow rate through the blood vessel or a decrease in a vascular resistance of the blood vessel.

9. The method of claim 1, wherein the one or more electrodes includes a first electrode and a second electrode, and wherein obtaining the measurement related to the blood flow rate comprises:
    detecting, at a first time, a first change in impedance in the blood vessel at the first electrode; and
    detecting, at a second time, a second change in the impedance in the blood vessel at the second electrode.

10. The method of claim 9,
    wherein the indicator fluid has a resistivity different than a resistivity of the blood in the blood vessel,
    wherein flow of the indicator fluid past the first electrode causes the first change in the impedance, and
    wherein flow of the indicator fluid past the second electrode causes the second change in the impedance.

11. A neuromodulation system comprising:
    a catheter including a proximal portion and a distal portion, the distal portion configured for intravascular delivery to a blood vessel of a patient, wherein the distal portion is configured to deliver neuromodulation energy at a target site in the blood vessel and detect an impedance in the blood vessel; and
    a controller configured to:
        determine, using the catheter, a transient change in the impedance in the blood vessel resulting from an introduction of a bolus of an indicator fluid into the blood vessel upstream of the target site relative to a direction of blood flow in the blood vessel, the bolus having a known volume;
        determine a measurement related to a blood flow rate through the blood vessel based on the transient change in the impedance and the known volume;
        correct the measurement related to the blood flow rate for at least one of a current leakage into surrounding tissue of the blood vessel or a non-homogeneity of an impedance field across a cross-sectional area of the blood vessel, wherein correcting the measurement is based on a flow rate offset and a flow rate gain term;
        compare the measurement related to the flood flow rate to a baseline measurement related to the blood flow rate through the blood vessel; and
        based on the comparison, determine a change in the blood flow rate through the blood vessel resulting from neuromodulation energy delivered via the catheter.

12. The neuromodulation system of claim 11, further comprising a guide catheter configured to be intravascularly positioned within the patent, wherein the guide catheter includes a lumen configured to receive the catheter therethrough and a distal guide catheter portion configured to deliver the indicator fluid into the blood vessel,
    wherein the guide catheter is configured to be intravascularly positioned within the patient upstream of the target site relative to the direction of blood flow in the blood vessel, and
    wherein the indicator fluid has a resistivity different than a resistivity of the blood in the blood vessel.

13. The neuromodulation system of claim 11, further comprising an injector mechanism in fluid communication with the catheter, wherein the injector mechanism is configured to inject the indicator fluid into the blood vessel such that the indicator fluid flows past the distal portion of the catheter.

14. The neuromodulation system of claim 11, wherein the indicator fluid has a resistivity different than a resistivity of the blood in the blood vessel.

15. The neuromodulation system of claim 11, wherein the distal portion of the catheter includes a first electrode and a second electrode, and wherein the controller is configured to determine a time difference between detection of the transient impedance change at the first electrode and the second electrode.

16. The neuromodulation system of claim 11, wherein the controller is configured to determine the blood flow rate through the blood vessel based at least in part on a summation of the transient impedance change over time.

17. The neuromodulation system of claim 11, wherein the controller is configured to determine the transient change in the impedance in the blood vessel by at least:
    determining an indicator-dilution curve from a first time corresponding to when the indicator fluid begins to flow past one or more electrodes of the catheter to a second time corresponding to when the indicator fluid has passed downstream of the one or more electrodes; and
    integrating the indicator-dilution curve.

18. The neuromodulation system of claim 11, wherein to compare the measurement related to the blood flow rate to the baseline measurement, the controller is configured to determine at least one of an increase in the blood flow rate through the blood vessel or a decrease in a vascular resistance of the blood vessel.

19. A method for assessing efficacy of neuromodulation therapy, the method comprising:
- positioning a distal portion of a neuromodulation catheter at a target site within a blood vessel of a patient, wherein the distal portion of the neuromodulation catheter is configured to deliver neuromodulation energy;
- injecting a first bolus of an indicator fluid into the blood vessel, wherein the indicator fluid has a resistivity that is higher than a resistivity of blood in the blood vessel, the first bolus having a first known volume;
- determining a first transient change in an impedance in the blood vessel resulting from movement of the first bolus of the indicator fluid past the distal portion of the neuromodulation catheter;
- delivering neuromodulation energy at the target site with the neuromodulation catheter;
- injecting, after delivery of the neuromodulation energy, a second bolus of the indicator fluid into the blood vessel, the second bolus having a second known volume;
- determining a second transient change in the impedance in the blood vessel resulting from movement of the second bolus of the indicator fluid past the distal portion of the neuromodulation catheter;
- comparing the first and second transient changes in the impedance to assess the efficacy of the delivered neuromodulation energy,
- wherein comparing the first and second transient changes in the impedance includes determining at least one of an increase in a flow rate of the blood in the blood vessel or a decrease in vascular resistance of the blood vessel; and
- correcting the determined increase in the flow rate of the blood for at least one of a current leakage into surrounding tissue of the blood vessel or a non-homogeneity of an impedance field across a cross-sectional area of the blood vessel, wherein correcting the determined increase in the flow rate is based on a flow rate offset and a flow rate gain term.

20. The method of claim 19, further comprising again delivering neuromodulation energy at the target site with the neuromodulation catheter when at least one of the increase in flow rate or the decrease in vascular resistance are below a predetermined threshold.

* * * * *